United States Patent
Kikuchi et al.

(10) Patent No.: US 11,209,359 B2
(45) Date of Patent: Dec. 28, 2021

(54) APPARATUS AND METHOD FOR MEASURING FLUID INFORMATION FROM LIGHT SCATTERING

(71) Applicants: PIONEER CORPORATION, Tokyo (JP); NIKKISO COMPANY LIMITED, Tokyo (JP)

(72) Inventors: Ikuya Kikuchi, Saitama (JP); Atsuya Ito, Saitama (JP); Ryohei Kagawa, Saitama (JP); Tomoya Murakami, Shizuoka (JP); Akari Agata, Shizuoka (JP); Genki Adachi, Shizuoka (JP)

(73) Assignees: PIONEER CORPORATION, Tokyo (JP); NIKKISO COMPANY LIMITED, Tokyo (JP)

( * ) Notice: Subject to any disclaimer, the term of this patent is extended or adjusted under 35 U.S.C. 154(b) by 0 days.

(21) Appl. No.: 16/651,563

(22) PCT Filed: Sep. 29, 2017

(86) PCT No.: PCT/JP2017/035678
§ 371 (c)(1),
(2) Date: Mar. 27, 2020

(87) PCT Pub. No.: WO2019/064559
PCT Pub. Date: Apr. 4, 2019

(65) Prior Publication Data
US 2020/0264100 A1    Aug. 20, 2020

(51) Int. Cl.
*G01N 21/53* (2006.01)
*G01N 33/49* (2006.01)

(52) U.S. Cl.
CPC .......... *G01N 21/532* (2013.01); *G01N 33/49* (2013.01); *G01N 2201/06113* (2013.01)

(58) Field of Classification Search
CPC ................ G01N 21/532; G01N 33/49; G01N 2201/06113; G01N 2021/4707;
(Continued)

(56) References Cited

U.S. PATENT DOCUMENTS 5,166,537 A * 11/1992 Horiuchi ............ G01N 15/1227
250/573
5,506,679 A * 4/1996 Cooper ................... G01N 21/53
356/338

(Continued)

FOREIGN PATENT DOCUMENTS

JP        09-33423      2/1997
JP        2000-046722   2/2000
(Continued)

OTHER PUBLICATIONS

International Search Report, PCT/JP2017/035678, dated Dec. 19, 2017.
(Continued)

*Primary Examiner* — Roy M Punnoose
(74) *Attorney, Agent, or Firm* — Nixon & Vanderhye (57) ABSTRACT

A measuring apparatus is provided with: an irradiator configured to irradiate fluid with light; a first light receiver configured to receive a forward scatter component of scattered light scattered by the fluid; a second light receiver configured to receive a backscatter component of the scattered light; a third light receiver configured to receive a side scatter component of the scattered light; and an outputting device configured to output fluid information about the fluid, which is obtained on the basis of light receiving signals of the first light receiver, the second light receiver, and the third light receiver. According to this measuring apparatus, it is possible to output accurate fluid information because of the (Continued)

use of the forward scatter component, the backscatter component, and the side scatter component of the scattered light.

9 Claims, 7 Drawing Sheets

(58) Field of Classification Search
CPC ... G01N 2021/4726; G01N 2021/4769; G01N 2021/4711; G01N 2021/4709
USPC .......................................................... 356/446
See application file for complete search history.

(56) References Cited

U.S. PATENT DOCUMENTS

| | | | | |
|---|---|---|---|---|
| 5,604,590 | A * | 2/1997 | Cooper | G01N 21/53 356/338 |
| 6,510,330 | B1 | 1/2003 | Enejder | |
| 6,519,034 | B1 * | 2/2003 | Engler | G01N 21/532 250/574 |
| 6,567,166 | B2 * | 5/2003 | Ottens | G01N 21/532 356/343 |
| 6,743,634 | B2 * | 6/2004 | Kramer | G01N 15/1031 422/73 |
| 6,798,508 | B2 * | 9/2004 | Kramer | G01N 15/1459 356/338 |
| 6,869,569 | B2 * | 3/2005 | Kramer | G01N 15/1031 422/73 |
| 6,937,332 | B2 * | 8/2005 | Engler | G01N 21/532 356/338 |
| 7,390,662 | B2 * | 6/2008 | Riley | G01N 1/12 356/337 |
| 7,973,923 | B2 * | 7/2011 | Wynn | F16L 41/086 356/246 |
| 8,189,187 | B2 * | 5/2012 | Graham | C03B 23/04 356/246 |
| 2002/0159061 | A1 * | 10/2002 | Ottens | A47L 15/4297 356/338 |
| 2004/0036874 | A1 * | 2/2004 | Kramer | G01N 15/1459 356/342 |
| 2004/0038413 | A1 * | 2/2004 | Kramer | G01N 15/1459 436/63 |
| 2007/0058171 | A1 | 3/2007 | Berg et al. | |
| 2010/0290041 | A1 * | 11/2010 | Graham | C03B 23/04 356/246 |
| 2012/0031841 | A1 | 2/2012 | Zhang | |
| 2012/0062869 | A1 | 3/2012 | Bado et al. | |
| 2014/0339446 | A1 * | 11/2014 | Yamamoto | G01N 15/1434 250/576 |
| 2016/0271318 | A1 | 9/2016 | Wiktor et al. | |
| 2019/0212256 | A1 * | 7/2019 | Joch | G01N 21/53 |
| 2020/0225142 | A1 * | 7/2020 | Potenza | G01N 15/1459 |

FOREIGN PATENT DOCUMENTS

| | | |
|---|---|---|
| JP | 4451567 | 4/2010 |
| JP | 2016-540971 | 12/2016 |
| WO | WO 00/33053 | 6/2000 |
| WO | 02/068940 A1 | 9/2002 |
| WO | 2005/116636 A1 | 12/2005 |
| WO | 2013/114333 A1 | 8/2013 |

OTHER PUBLICATIONS

The extended European Search Report issued in European Patent Application No. 17927545.8 dated Apr. 21, 2021.

* cited by examiner

FIG. 7

APPARATUS AND METHOD FOR MEASURING FLUID INFORMATION FROM LIGHT SCATTERING

TECHNICAL FIELD

The present invention relates to a measuring apparatus and a measuring method that can measure information about fluid, a computer program, and a recording medium.

BACKGROUND ART

For this type of apparatus, there is known an apparatus configured to irradiate fluid with light and to receive scattered light, thereby measuring information about the fluid. In the fluid, irradiation light is scattered in a plurality of directions. If those scattered lights are separately detected, it is considered that the information about the fluid can be measured by using respective properties of the scattered lights (e.g., refer to Patent Literature 1).

CITATION LIST

Patent Literature

Patent Literature 1: Japanese Patent No. 4451567

SUMMARY OF INVENTION

Technical Problem

The scattered light may include not only forward scattered light and backscattered light, but also side scattered light (i.e., light scattered in a direction substantially perpendicular to an optical axis in a surface layer of the fluid). A method of measuring the information about the fluid by using the side scattered light, however, still has room for improvement. For example, in a technology/technique described in the Patent Literature 1, a change in components of the fluid may also change a relation among scatter components. Thus, in the measurement of fluids having different components, measurement precision is significantly reduced, which is technically problematic.

The above is an example of problems to be solved by the present invention. It is therefore an object of the present invention to provide a measuring apparatus and a measuring method that can measure the information about the fluid by using the side scattered light, a computer program, and a recording medium.

Solution to Problem

The above object of the present invention can be achieved by a first measuring apparatus provided with: an irradiator configured to irradiate fluid with light; a first light receiver configured to receive a forward scatter component of scattered light scattered by the fluid; a second light receiver configured to receive a backscatter component of the scattered light; a third light receiver configured to receive a side scatter component of the scattered light; and an outputting device configured to output fluid information about the fluid, which is obtained on the basis of light receiving signals of the first light receiver, the second light receiver, and the third light receiver.

The above object of the present invention can be achieved by a second measuring apparatus provided with: an irradiator configured to irradiate fluid with light; a first light receiver configured to receive a first component, which passes through the fluid, out of scattered light scattered by the fluid; a second light receiver configured to receive a second component, which is scattered in a first direction in which the irradiator is located in a surface layer of the fluid, out of the scattered light; a third light receiver configured to receive a third component, which is scattered in a second direction that is different from the first direction in the surface layer of the fluid, out of the scattered light; and an outputting device configured to output fluid information about the fluid, which is obtained on the basis of light receiving signals of the first light receiver, the second light receiver, and the third light receiver.

The above object of the present invention can be achieved by a measuring method provided with: an irradiating process of irradiating fluid with light; a first light receiving process of receiving a forward scatter component of scattered light scattered by the fluid; a second light receiving process of receiving a backscatter component of the scattered light; a third light receiving process of receiving a side scatter component of the scattered light; and an outputting process of outputting fluid information about the fluid, which is obtained on the basis of light receiving signals of the first light receiving process, the second light receiving process, and the third light receiving process.

The above object of the present invention can be achieved by a computer program for allowing a computer to perform: an irradiating process of irradiating fluid with light; a first light receiving process of receiving a forward scatter component of scattered light scattered by the fluid; a second light receiving process of receiving a backscatter component of the scattered light; a third light receiving process of receiving a side scatter component of the scattered light; and an outputting process of outputting fluid information about the fluid, which is obtained on the basis of light receiving signals of the first light receiving process, the second light receiving process, and the third light receiving process.

The above object of the present invention can be achieved by a recording medium on which the computer program described above is recorded.

DESCRIPTION OF EMBODIMENTS

<1>

A first measuring apparatus according to an embodiment is provided with: an irradiator configured to irradiate fluid with light; a first light receiver configured to receive a forward scatter component of scattered light scattered by the fluid; a second light receiver configured to receive a backscatter component of the scattered light; a third light receiver configured to receive a side scatter component of the scattered light; and an outputting device configured to output fluid information about the fluid, which is obtained on the basis of light receiving signals of the first light receiver, the second light receiver, and the third light receiver. According to the first measuring apparatus in the embodiment, in operation thereof, for example, the fluid that flows in a tubing is irradiated with light by the irradiator. The light irradiated or applied from the irradiator is scattered in the fluid and becomes the scattered light.

The scattered light is received by each of the plurality of receivers arranged in different positions. Specifically, the forward scatter component of the scattered light is received by the first light receiver, the backscatter component of the scattered light is received by the second light receiver, and the side scatter component of the scattered light is received by the third light receiver. From the light receiving signals of the first light receiver, the second light receiver, and the third light receiver, the fluid information about the fluid is obtained, and is outputted from the outputting device.

In the embodiment, as described above, at least three scatter components (i.e., the forward scatter component, the backscatter component, and the side scatter component) are used to obtain the fluid information. It is thus possible to output accurate fluid information, in comparison with that when the fluid information is obtained on the basis of only one or two scatter components.

Moreover, an example of the fluid in the embodiment is blood, but the measurement can be also applied to any fluid other than the blood (e.g., ink, oil, wastewater or sewage, a seasoning, etc.).

Furthermore, an example of the fluid information in the embodiment may be information about the concentration of the fluid. More specifically, the fluid information may be information about a numerical value indicating a ratio of the volume of blood cells or blood corpuscles in the blood (which is a so-called hematocrit value).

<2>

In an aspect of the measuring apparatus according to the embodiment, the outputting device is configured to output the fluid information, which is obtained on the basis of a sum of the backscatter component and the side scatter component, and on the basis of the forward scatter component.

According to studies by the present inventors, it is found that there is a fixed relation between the sum of the backscatter component and the side scatter component, and the forward scatter component. It is thus possible to output the accurate fluid information, more easily, by using the sum of the backscatter component and the side scatter component, and by using the forward scatter component.

<3>

In another aspect of the measuring apparatus according to the embodiment, the irradiator is placed such that an optical axis of irradiation light is diagonal to a direction in which the fluid flows.

According to this aspect, since oblique light is applied with respect to the direction in which the fluid flows, it is easy to place the third light receiver configured to receive the side scatter component. It is also easy to detect a Doppler signal.

<4>

In the aforementioned aspect in which the irradiator is placed such that the optical axis is diagonal, the irradiator may be placed such that the optical axis of the irradiation light is at an angle other than a vicinity of 45 degrees to the direction in which the fluid flows.

If the light is irradiated or applied at an angle of the vicinity of 45 degrees to the direction in which the fluid flows, strong scattered light, which includes the backscatter component, enters the third light receiver configured to receive the side scattered light, and it is hardly possible to appropriately receive the side scatter component. If the light is irradiated or applied at the angle other than the vicinity of 45 degrees, the aforementioned detrimental effect can be avoided.

<5>

In another aspect of the measuring apparatus according to the embodiment, the irradiator includes a first irradiator and a second irradiator, the first light receiver is configured to receive a forward scatter component of scattered light of the first irradiator; the second light receiver is configured to receive a backscatter component of the scattered light of the first irradiator; and the third light receiver is configured to receive a side scatter component of scattered light of the second irradiator.

According to this aspect, the first irradiator for generating the forward scatter component and the backscatter component and the second irradiator for generating the side scatter component are provided, separately. Thus, in comparison with a single irradiator, it is possible to make measurements in the conditions that are suitable for the respective scatter components.

<6>

A second measuring apparatus according to an embodiment is provided with: an irradiator configured to irradiate fluid with light; a first light receiver configured to receive a first component, which passes through the fluid, out of scattered light scattered by the fluid; a second light receiver configured to receive a second component, which is scattered in a first direction in which the irradiator is located in a surface layer of the fluid, out of the scattered light; a third light receiver configured to receive a third component, which is scattered in a second direction that is different from the first direction in the surface layer of the fluid, out of the scattered light; and an outputting device configured to output fluid information about the fluid, which is obtained on the basis of light receiving signals of the first light receiver, the second light receiver, and the third light receiver.

According to the second measuring apparatus in the embodiment, the first component, which passes through the fluid, is received by the first light receiver, the second component, which is scattered in the first direction in which the irradiator is located in the surface layer of the fluid, is received by the second light receiver, and the third component, which is scattered in the second direction that is different from the first direction in the surface layer of the fluid, is received by the third light receiver. From the light receiving signals of the first light receiver, the second light receiver, and the third light receiver, the fluid information about the fluid is obtained, and is outputted from the outputting device.

In the embodiment, as described above, at least three scatter components (i.e., the first component, the second component, and the third component) are used to obtain the fluid information. It is thus possible to output the accurate fluid information, in comparison with that when the fluid information is obtained on the basis of only one or two scatter components.

<7>

A measuring method according to an embodiment is a measuring method provided with: an irradiating process of irradiating fluid with light; a first light receiving process of receiving a forward scatter component of scattered light scattered by the fluid; a second light receiving process of receiving a backscatter component of the scattered light; a third light receiving process of receiving a side scatter component of the scattered light; and an outputting process of outputting fluid information about the fluid, which is obtained on the basis of light receiving signals of the first light receiving process, the second light receiving process, and the third light receiving process.

According to the measuring method in the embodiment, as in the measuring apparatus described above, at least three scatter components are used to obtain the fluid information. It is thus possible to output the accurate fluid information, in comparison with that when the fluid information is obtained on the basis of only one or two scatter components.

<8>

A computer program according to an embodiment allows a computer to perform: an irradiating process of irradiating fluid with light; a first light receiving process of receiving a forward scatter component of scattered light scattered by the fluid; a second light receiving process of receiving a backscatter component of the scattered light; a third light receiving process of receiving a side scatter component of the scattered light; and an outputting process of outputting fluid information about the fluid, which is obtained on the basis of light receiving signals of the first light receiving process, the second light receiving process, and the third light receiving process.

According to the computer program in the embodiment, the computer is allowed to perform the same processes as those in the measuring method described above. It is thus possible to output the accurate fluid information.

<9>

On a recording medium according to an embodiment, the computer program described above is recorded.

According to the recording medium in the embodiment, the stored computer program can be executed by the computer. It is thus possible to output the accurate fluid information.

The effect and other benefits of the measuring apparatus, the measuring method, the computer program, and the recording medium according to the embodiments will be explained in more detail in practical examples below.

PRACTICAL EXAMPLES

Hereinafter, a measuring apparatus according to practical examples will be explained in detail with reference to the drawings. In the following, an explanation will be given to a situation in which the measuring apparatus is applied to an apparatus for measuring the concentration (or a hematocrit value) of blood that flows in a tubing that constitutes a blood circuit of an artificial dialysis apparatus.

First Practical Example

Figure 1:
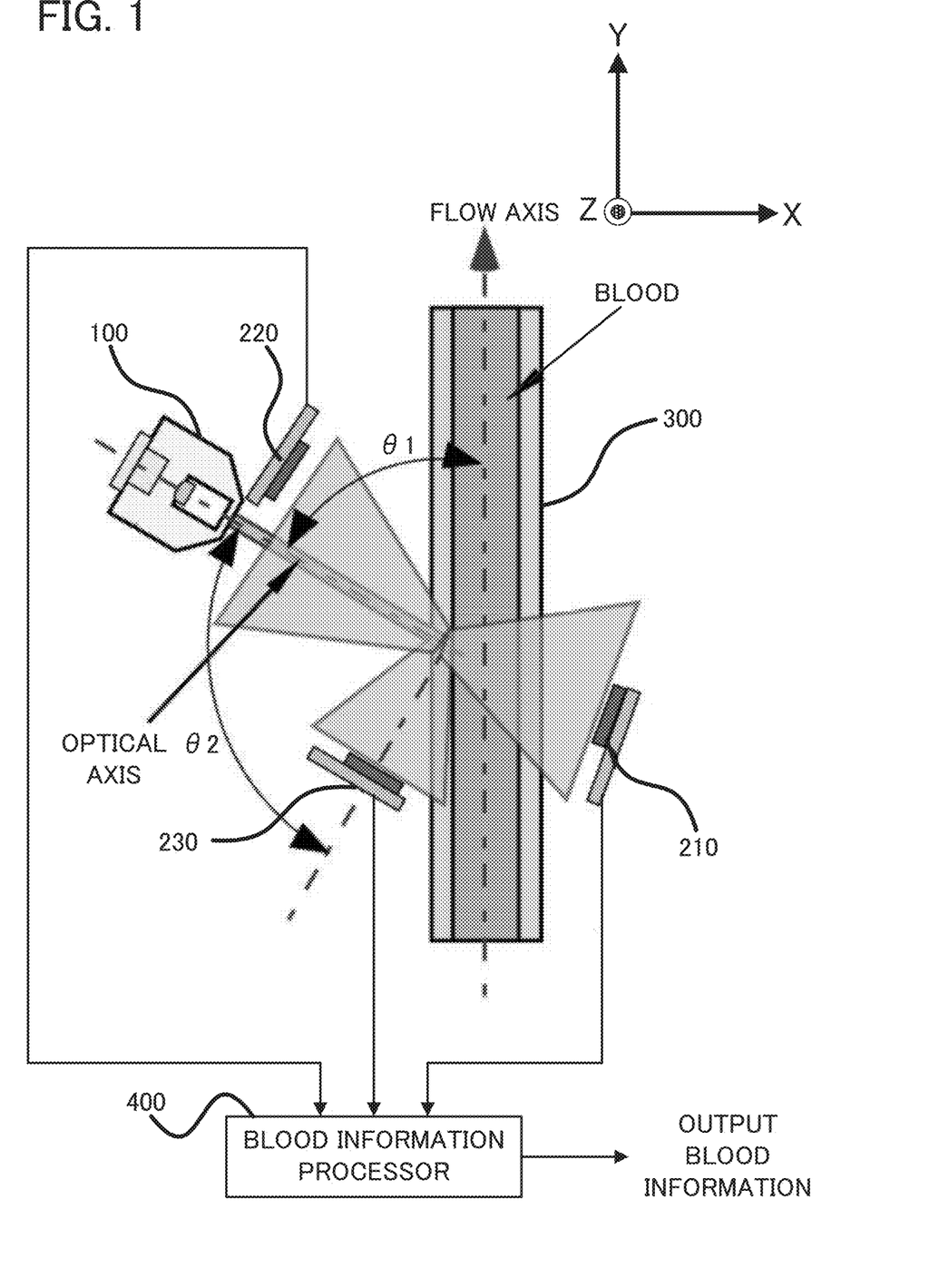
FIG. 1 is a plan view illustrating a configuration of a measuring apparatus according to a first practical example.

Firstly, a configuration of the measuring apparatus according to a first practical example will be explained with reference to FIG. 1. FIG. 1 is a plan view illustrating the configuration of the measuring apparatus according to the first practical example.

As illustrated in FIG. 1, the measuring apparatus according to the first practical example is configured as an apparatus for measuring a hematocrit value of blood by irradiating the blood that flows in a tubing 300, with light. The measuring apparatus is provided with an irradiator 100, a first light receiver 210, a second light receiver 220, a third light receiver 230, and a blood information processor 400.

The irradiator 100 is configured, for example, as a laser light source, and is configured to irradiate the blood that flows in the tubing 300, with light. The irradiator 100 is placed such that an optical axis of irradiation light is an angle of θ1 to a direction in which the blood flows (i.e., a flow axis in FIG. 1). θ1 may be an angle other than the vicinity of 90 degrees and the vicinity of 45 degrees. The reason of avoiding setting θ1 in the vicinity of 90 degrees is to facilitate the placement of the third light receiver 230 described later. The reason of avoiding setting θ1 in the vicinity of 45 degrees is to prevent strong scattered light, which includes a backscatter component, from entering the third light receiver 230 described later.

The first light receiver 210 is placed in a position in which it can receive a component that passes through the blood (i.e., a forward scatter component), out of light scattered by the blood that flows in the tubing 300. Specifically, the first light receiver 210 is placed in a position opposite to the irradiator 100, as viewed from the tubing 300. The first light receiver 210 is configured to output a signal corresponding to the received forward scatter component, to the blood information processor 400.

The second light receiver 220 is placed in a position in which it can receive a component that is scattered in a direction of the position of the irradiator 100 (i.e., a backscatter component), out of the light scattered by the blood that flows in the tubing 300. Specifically, the second light receiver 220 is placed in a position extremely close to the irradiator 100. The second light receiver 220 is configured to output a signal corresponding to the received backscatter component, to the blood information processor 400.

The third light receiver 230 is placed in a position in which it can receive a component that is scattered in a direction that is different from the direction of the position of the irradiator 100 (i.e., a side scatter component), out of the light scattered by the blood that flows in the tubing 300. Specifically, the third light receiver 230 is placed in a direction at an angle of θ2 to the optical axis of irradiation light. θ2 is in the vicinity of 90 degrees.

The blood information processor 400 is configured to arithmetically operate and output blood information (which is herein the hematocrit value of the blood), on the basis of the light receiving signals inputted from the first light receiver 210, the second light receiver 220, and the third light receiver 230. A method of arithmetically operating the blood information will be detailed later.

Figure 2:
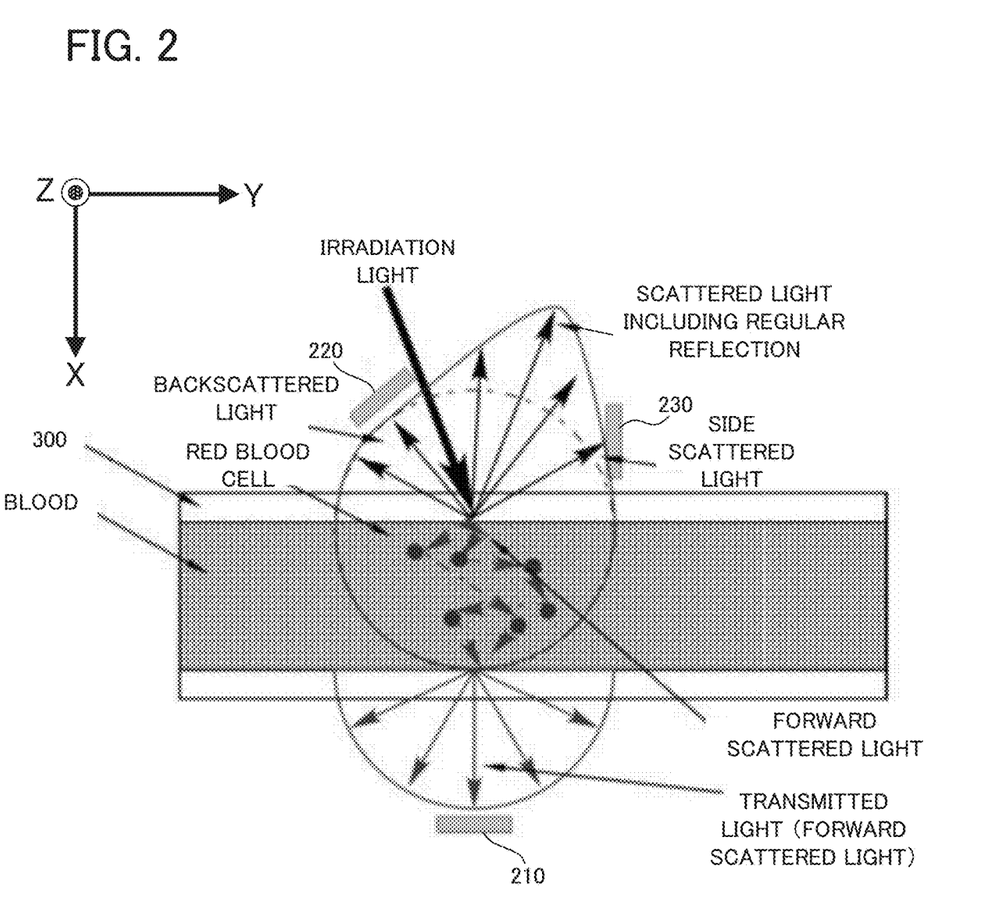
FIG. 2 is version 1 of a cross sectional view illustrating a plurality of scatter components of irradiation light and a placement location of each light receiver.
Figure 3:
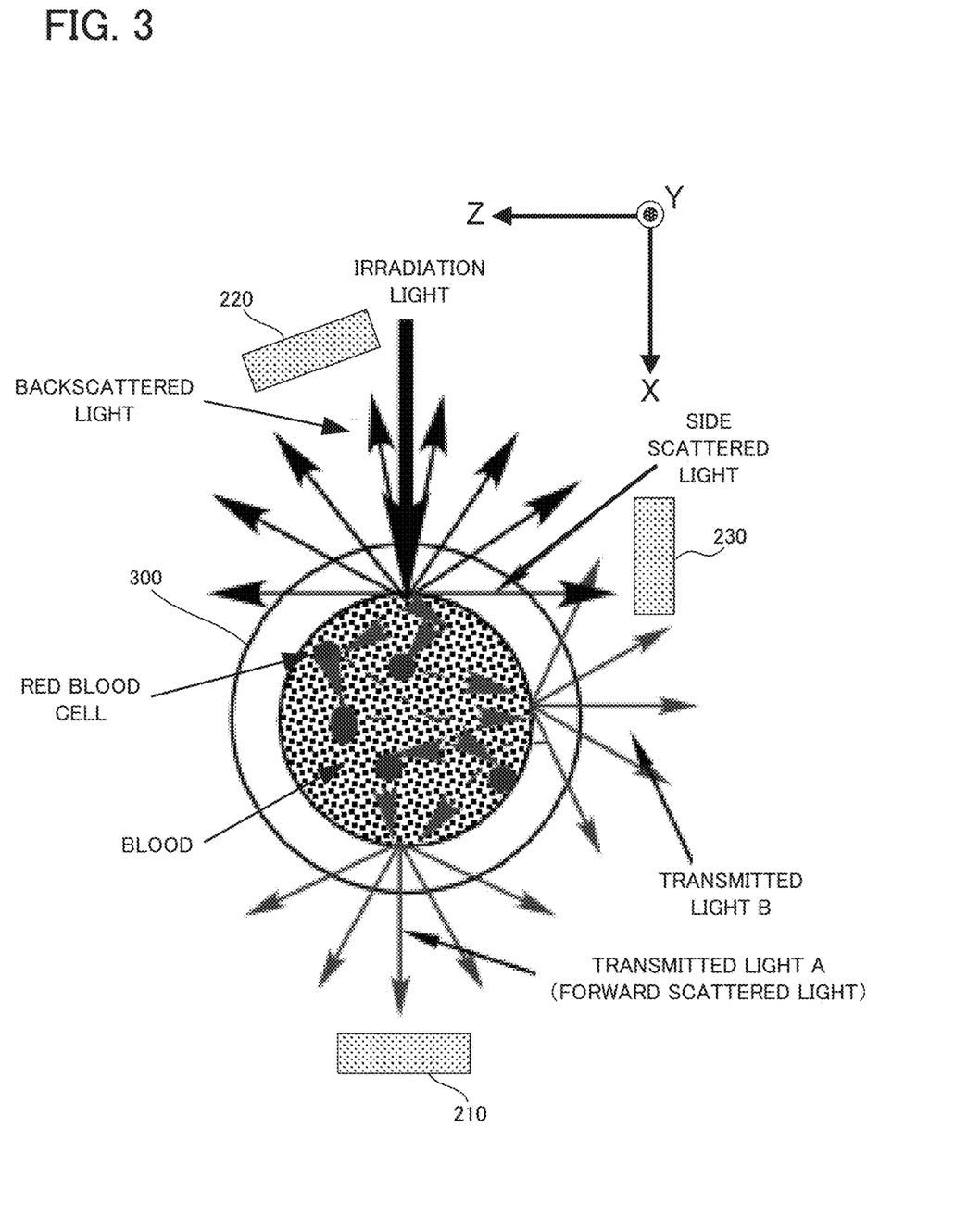
FIG. 3 is version 2 of a cross sectional view illustrating a plurality of scatter components of irradiation light and a placement location of each light receiver.

For convenience of explanation, in FIG. 1, a positional relation of the light receivers is illustrated, two-dimensionally, but the light receivers may be arranged, three-dimensionally. Hereinafter, a three-dimensional arrangement of the first light receiver 210, the second light receiver 220, and the third light receiver 230 will be explained with reference to FIG. 2 and FIG. 3. FIG. 2 is version 1 of a cross sectional view illustrating a plurality of scatter components of the irradiation light and a placement location of each light receiver. FIG. 3 is version 2 of a cross sectional view illustrating a plurality of scatter components of irradiation light and a placement location of each light receiver.

Each of coordinate axes in FIG. 2 and FIG. 3 corresponds to a coordinate axis in FIG. 1. In other words, FIG. 2 is a cross sectional view in a direction in which the blood flows from a left side to a right side in the drawing. FIG. 3 is a cross sectional view in a direction in which the blood flows from a far side to a near side in the drawing.

As illustrated in FIG. 2 and FIG. 3, each of various components of the scattered light (i.e., the forward scatter component, the backscatter component, and the side scatter component) spreads from a scattering point (which is specifically a surface layer of the blood), three-dimensionally and radially. Thus, even when the first light receiver 210, the second light receiver 220, and the third light receiver 230 are arranged, three-dimensionally, as illustrated in FIG. 2 and FIG. 3, the light receivers can receive the respective scatter components. This three-dimensional arrangement increases the degree of freedom of an arrangement layout of the light receivers.

Figure 4:
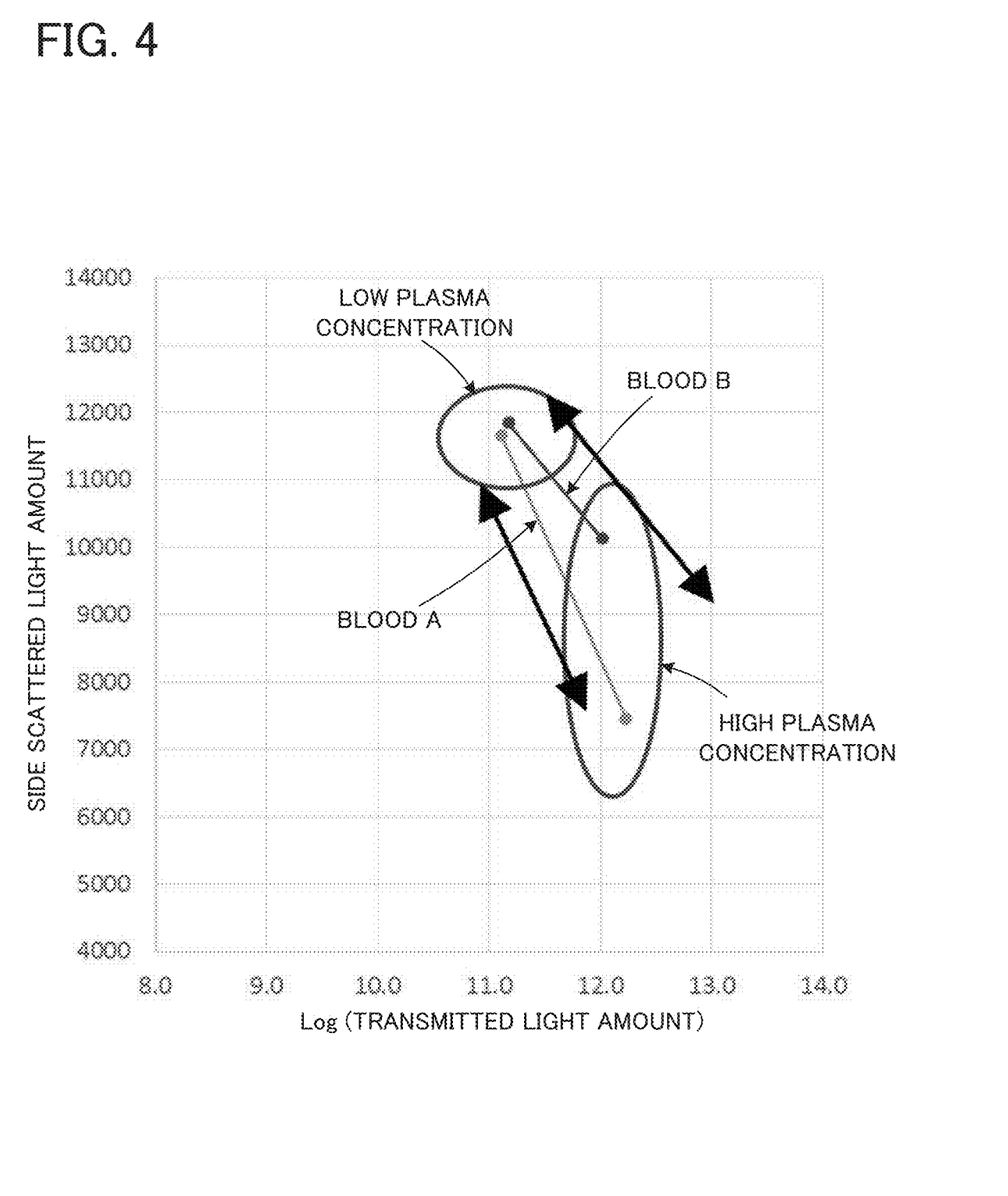
FIG. 4 is a graph illustrating a relation between a transmitted light amount and a side scattered light amount.
Figure 5:
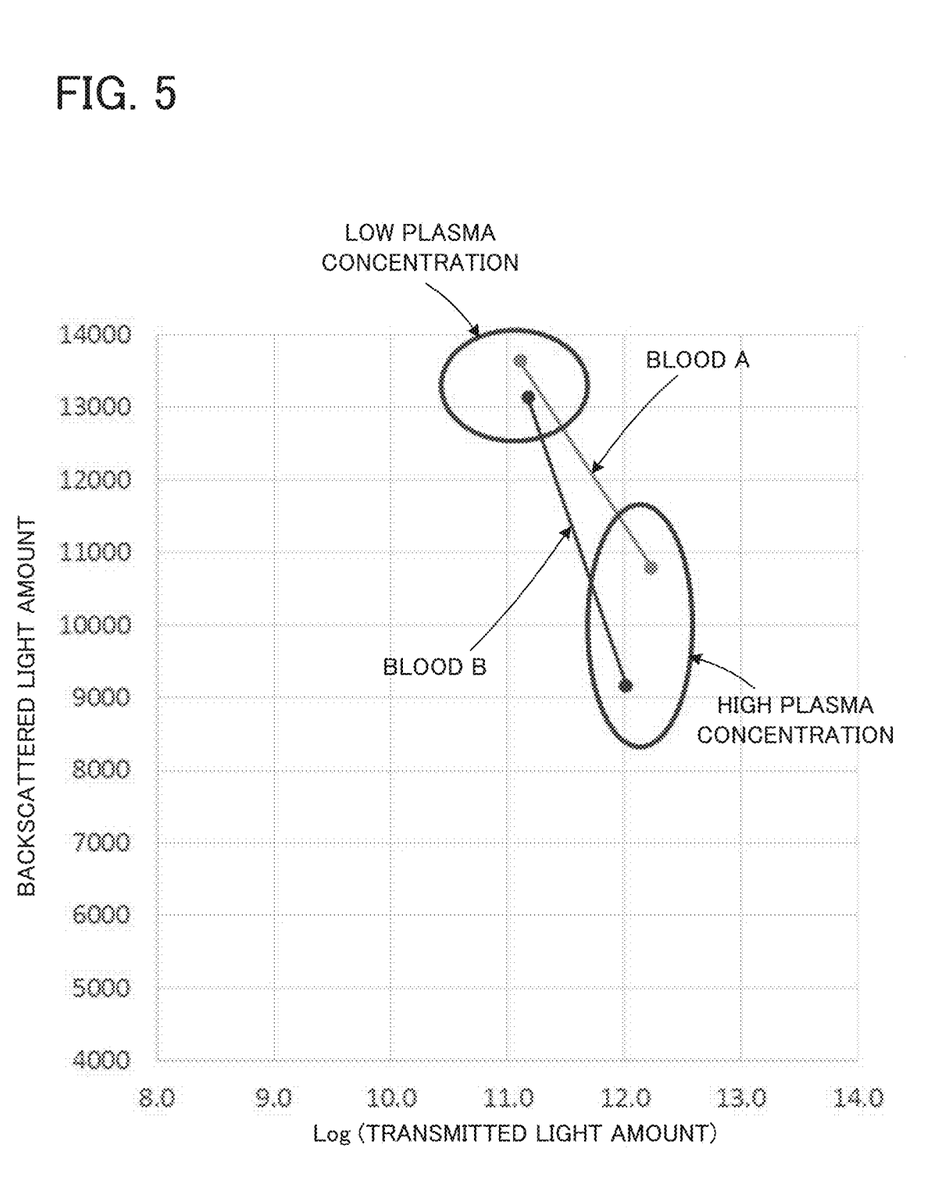
FIG. 5 is a graph illustrating a relation between the transmitted light amount and a backscattered light amount.

Next, a relation among the scatter components and a resulting problem thereof will be explained with reference to FIG. 4 and FIG. 5. FIG. 4 is a graph illustrating a relation between a transmitted light amount and a side scattered light amount. FIG. 5 is a graph illustrating a relation between the transmitted light amount and a backscattered light amount.

As illustrated in FIG. 4, a relation between an amount of light received by the first light receiver 210 (hereinafter referred to a "transmitted light amount" as occasion demands) and an amount of light received by the third light receiver 230 (hereinafter referred to a "side scattered light amount" as occasion demands) changes between when protein concentration in blood plasma in the blood is high and when it is low. Specifically, when the protein concentration in the blood plasma changes, a relation between a logarithm of the transmitted light amount (Log transmitted light amount) and the side scattered light amount linearly changes. At this time, a slope of a straight line varies depending on the type of the blood. As is clear from the drawing, a slope of a straight line of the blood A is clearly different from that of the blood B.

As illustrated in FIG. 5, a relation between the amount of the light received by the first light receiver 210 (i.e., the transmitted light amount) and an amount of light received by the second light receiver 220 (hereinafter referred to a "backscattered light amount" as occasion demands) also changes between when the protein concentration in the blood plasma in the blood is high and when it is low. Specifically, when the protein concentration in the blood plasma changes, a relation between the logarithm of the transmitted light amount (Log transmitted light amount) and the backscattered light amount linearly changes. At this time, a slope of a straight line varies depending on the type of the blood. As is clear from the drawing, a slope of a straight line of the blood A is clearly different from that of the blood B.

The results in FIG. 4 and FIG. 5 may mean that the hematocrit value cannot be accurately measured from the transmitted light amount and the side scattered light amount, or from the transmitted light amount and the backscattered light amount. In order to solve the problem, the measuring apparatus according to the first practical example is configured to calculate the hematocrit value by using the three types of scatter components.

Figure 6:
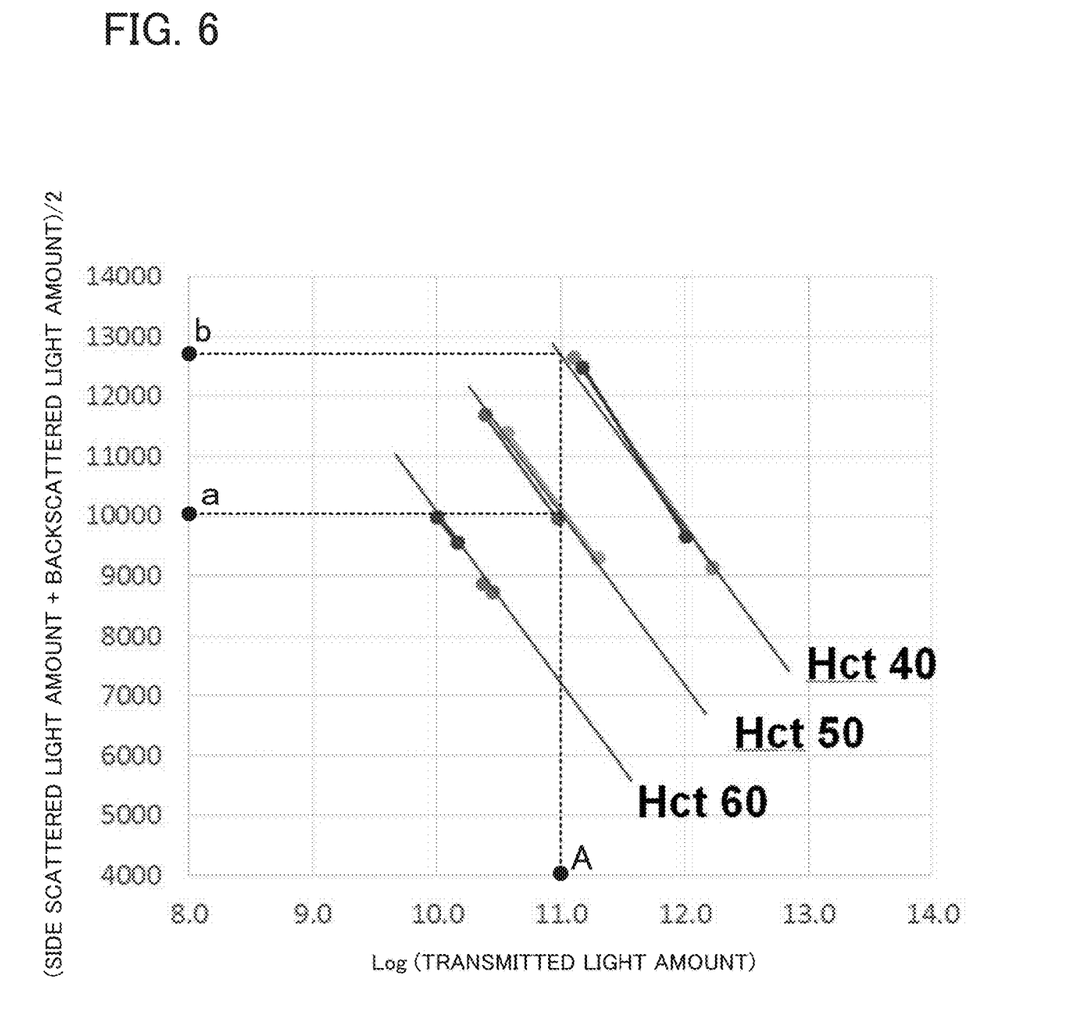
FIG. 6 is a graph illustrating a relation between the transmitted light amount and a sum of the side scattered light amount and the backscattered light amount.

Next, a method of deriving the hematocrit value by the measuring apparatus according to the first practical example will be explained with reference to FIG. 6. FIG. 6 is a graph illustrating a relation between the transmitted light amount and a sum of the side scattered light amount and the backscattered light amount (or an average value of the side scattered light amount and the backscattered light amount).

As illustrated in FIG. 6, according to studies by the present inventors, it is found that there is a fixed relation between the transmitted light amount and the sum of the side scattered light amount and the backscattered light amount. Specifically, when the transmitted light amount is L1, the side scattered light amount is L2, and the backscattered light amount, the following relation is established.

$$\alpha \times L2 + \beta \times L3 \propto \text{Log } L1 : (\alpha \times \beta \neq 0),$$

wherein $\alpha$ and $\beta$ are predetermined gain coefficients.

As a result, by measuring each of the transmitted light amount, the side scattered light amount, and the backscattered light amount, the hematocrit value can be arithmetically operated by using the above relation. The hematocrit value may be arithmetically operated by using a predetermined mathematical expression, or may be determined by preparing a map as illustrated in FIG. 6 in advance.

For example, when the transmitted light amount (i.e., Log L1) is A, if the sum of the side scattered light amount and the backscattered light amount (i.e., $(\alpha \times L2 + \beta \times L3)/2$) is a, then, the hematocrit value can be determined to be Hct=50. When the transmitted light amount (i.e., Log L1) is A, if the sum of the side scattered light amount and the backscattered light amount (i.e., $(\alpha \times L2 \pm \beta \times L3)/2$) is b, then, the hematocrit value can be determined to be Hct=40.

As explained above, according to the measuring apparatus in the first practical example, it is possible to arithmetically operate an accurate hematocrit value, by measuring each of the transmitted light amount (i.e., the forward scatter component of the scattered light), the side scattered light amount (i.e., the side scatter component of the scattered light), and the backscattered light amount (i.e., the backscatter component of the scattered light).

Second Practical Example

Figure 7:
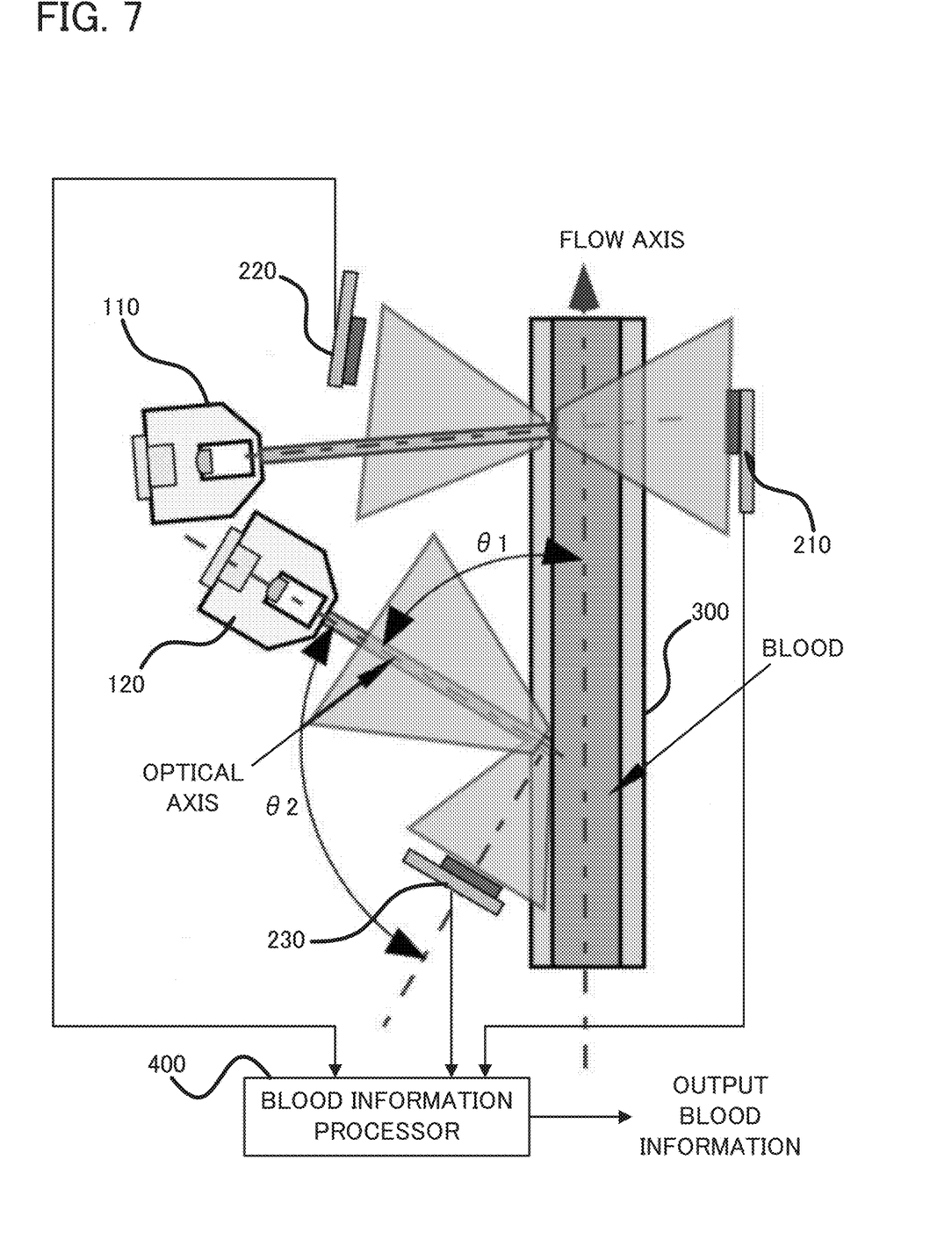
FIG. 7 is a plan view illustrating a configuration of a measuring apparatus according to a second practical example.

Next, a measuring apparatus according to a second practical example will be explained with reference to FIG. 7. FIG. 7 is a plan view illustrating a configuration of the measuring apparatus according to the second practical example.

The second practical example is partially different in configuration from the first practical example described above, and is substantially the same in other part. Thus, hereinafter, only a different part from the first practical example will be explained in detail, and an explanation of the same part will be omitted, as occasion demands.

As illustrated in FIG. 7, the measuring apparatus according to the second practical example is provided with two irradiators (which are specifically a first irradiator 110 and a second irradiator 120).

The first irradiator 110 is configured to apply light for measuring the transmitted light amount and the backscattered light amount. Thus, the first light receiver 210, which is configured to receive the forward scatter component, is placed opposite to the first irradiator 110, as viewed from the tubing 300, and the second light receiver 220, which is configured to receive the backscatter component, is placed extremely close to the first irradiator 110.

The second irradiator 120 is configured to apply light for measuring the side scattered light amount. Thus, the second irradiator 120 is placed such that an optical axis of irradiation light is an angle of θ1 to a direction in which the blood flows (i.e., a flow axis). Moreover, the third light receiver 230 is placed in a direction at an angle of θ2 to the optical axis of the light applied by the second irradiator 120.

According to the measuring apparatus in the second practical example, the provision of the two irradiators makes it possible to realize measurement conditions corresponding to the respective scatter components. Specifically, by placing the first irradiator 110 such that the light applied by the first irradiator 110 enters substantially perpendicular to the flow axis while diagonally setting the optical axis of the second irradiator 120 for measuring the side scattered light amount, it is possible to narrow a scattering range of the transmitted light, in comparison with that when the optical axis of the first irradiator 110 is diagonally set, so that it is possible to miniaturize the first irradiator 110.

The present invention is not limited to the aforementioned embodiments and examples, but various changes may be made, if desired, without departing from the essence or spirit of the invention which can be read from the claims and the entire specification. A measuring apparatus, a measuring method, a computer program, and a recording medium that involve such changes are also intended to be within the technical scope of the present invention.

DESCRIPTION OF REFERENCE NUMERALS AND LETTERS 100 irradiator
110 first irradiator
120 second irradiator
210 first light receiver
220 second light receiver
230 third light receiver
300 tubing
400 blood information processor

The invention claimed is:

1. A measuring apparatus, comprising:
an irradiator configured to irradiate fluid with light;
a first light receiver configured to receive a forward scatter component of scattered light scattered by the fluid;
a second light receiver configured to receive a backscatter component of the scattered light;
a third light receiver configured to receive a side scatter component of the scattered light; and
an outputter configured to output fluid information about the fluid, which is obtained on the basis of light receiving signals of said first light receiver, said second light receiver, and said third light receiver,
wherein the fluid information output by said outputter is obtained on the basis of a sum of the backscatter component and the side scatter component, and on the basis of the forward scatter component.

2. The measuring apparatus according to claim 1, wherein said irradiator is placed such that an optical axis of irradiation light is diagonal to a direction in which the fluid flows.

3. The measuring apparatus according to claim 2, wherein said irradiator is placed such that the optical axis of the irradiation light is at an angle other than a vicinity of 45 degrees to the direction in which the fluid flows.

4. The measuring apparatus according to claim 3, wherein:
said irradiator includes a first irradiator and a second irradiator,
said first light receiver is configured to receive a forward scatter component of scattered light of the first irradiator;
said second light receiver is configured to receive a backscatter component of the scattered light of the first irradiator; and
said third light receiver is configured to receive a side scatter component of scattered light of the second irradiator.

5. The measuring apparatus according to claim 2, wherein:
said irradiator includes a first irradiator and a second irradiator,
said first light receiver is configured to receive a forward scatter component of scattered light of the first irradiator;
said second light receiver is configured to receive a backscatter component of the scattered light of the first irradiator; and
said third light receiver is configured to receive a side scatter component of scattered light of the second irradiator.

6. The measuring apparatus according to claim 1, wherein:
said irradiator includes a first irradiator and a second irradiator,
said first light receiver is configured to receive a forward scatter component of scattered light of the first irradiator;
said second light receiver is configured to receive a backscatter component of the scattered light of the first irradiator; and
said third light receiver is configured to receive a side scatter component of scattered light of the second irradiator.

7. A measuring apparatus, comprising:
an irradiator configured to irradiate fluid with light;
a first light receiver configured to receive a first component, which passes through the fluid, out of scattered light scattered by the fluid;
a second light receiver configured to receive a second component, which is scattered in a surface layer of the fluid and scattered in a first direction in which said irradiator is located, out of the scattered light;
a third light receiver configured to receive a third component, which is scattered in a second direction that is different from the first direction in the surface layer of the fluid, out of the scattered light; and
an outputter configured to output fluid information about the fluid, which is obtained on the basis of light receiving signals of said first light receiver, said second light receiver, and said third light receiver.

8. A measuring method, comprising:
irradiating fluid with light;
receiving a forward scatter component of scattered light scattered by the fluid;
receiving a backscatter component of the scattered light;
receiving a side scatter component of the scattered light; and
an outputting process of outputting fluid information about the fluid, which is obtained on the basis of light receiving signals of the forward scatter component, the backscatter component, and the side scatter component,
wherein the fluid information is obtained on the basis of a sum of the backscatter component and the side scatter component, and on the basis of the forward scatter component.

9. A non-transitory computer-readable medium on which is stored a program which, when executed by a computer, causes the computer to perform:
irradiating fluid with light;
receiving a forward scatter component of scattered light scattered by the fluid;
receiving a backscatter component of the scattered light;
receiving a side scatter component of the scattered light; and outputting fluid information about the fluid, which is obtained on the basis of light receiving signals of the forward scatter component, the backscatter component, and the side scatter component,
wherein the fluid information is obtained on the basis of a sum of the backscatter component and the side scatter component, and on the basis of the forward scatter component.

* * * * *